US009504575B2

(12) United States Patent
Kaplan et al.

(10) Patent No.: US 9,504,575 B2
(45) Date of Patent: Nov. 29, 2016

(54) 3-DIMENSIONAL SILK HYDROXYAPATITE COMPOSITIONS

(75) Inventors: David L. Kaplan, Concord, MA (US); Hyeon Joo Kim, Cupertino, CA (US); Gerard Kugel, Lexington, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 12/866,256

(22) PCT Filed: Feb. 6, 2009

(86) PCT No.: PCT/US2009/033309
§ 371 (c)(1), (2), (4) Date: Nov. 4, 2010

(87) PCT Pub. No.: WO2009/100280
PCT Pub. Date: Aug. 13, 2009

(65) Prior Publication Data

US 2011/0046686 A1 Feb. 24, 2011

Related U.S. Application Data

(60) Provisional application No. 61/026,896, filed on Feb. 7, 2008, provisional application No. 61/085,569, filed on Aug. 1, 2008.

(51) Int. Cl.
*A61F 2/46* (2006.01)
*A61F 2/28* (2006.01)
(Continued)

(52) U.S. Cl.
CPC .............. *A61F 2/2846* (2013.01); *A61L 27/46* (2013.01); *A61L 27/54* (2013.01); *A61F 2002/2817* (2013.01); *A61F 2310/00293* (2013.01); *A61F 2310/00365* (2013.01);
(Continued)

(58) Field of Classification Search
USPC .......................... 606/86 R; 623/17.11–17.16
See application file for complete search history.

(56) References Cited

U.S. PATENT DOCUMENTS 1,989,005 A 1/1935 Fink et al.
4,233,212 A 11/1980 Otoi et al.
(Continued)

FOREIGN PATENT DOCUMENTS

CA 2405850 10/2002
CN 1078509 A 11/1993
(Continued)

OTHER PUBLICATIONS

Renugopalakrishnan, Bionanotechnology: Proteins to Nanodevices, 2006, Dordrecht: Springer, p. 202.*
(Continued)

*Primary Examiner* — Nicholas Woodall
(74) *Attorney, Agent, or Firm* — Choate, Hall & Stewart, LLP

(57) ABSTRACT

Described herein are methods and compositions comprising a mixture of silk polymer and hydroxyapatite. The methods described herein can be used to prepare a mixture of silk polymer and hydroxyapatite and further provide mixtures that can be molded into a desired shape. Also encompassed herein are compositions comprising a mixture of silk polymer and hydroxyapatite having a desired shape, which can further be implanted, for example, to facilitate bone healing or tooth structure or support. Such compositions can also include agents, such as therapeutic agents, or cells.

13 Claims, 6 Drawing Sheets

Prototype of cylindrical 30% HA mineralized silk polymer with 2% raw fiber

(51) Int. Cl.
*A61L 27/46* (2006.01)
*A61L 27/54* (2006.01)

(52) U.S. Cl.
CPC ... *A61L 2300/414* (2013.01); *A61L 2300/602* (2013.01); *A61L 2300/64* (2013.01); *A61L 2430/02* (2013.01)

(56) References Cited

U.S. PATENT DOCUMENTS 4,820,418 A 4/1989 Hirotsu et al.
5,047,507 A 9/1991 Buchegger et al.
5,245,012 A 9/1993 Lombari et al.
5,252,285 A 10/1993 Lock
5,290,494 A 3/1994 Coombes et al.
5,606,019 A 2/1997 Cappello
5,728,810 A 3/1998 Lewis et al.
5,770,193 A 6/1998 Vacanti et al.
5,994,099 A 11/1999 Lewis et al.
6,027,742 A 2/2000 Lee et al.
6,110,590 A 8/2000 Zarkoob et al.
6,117,456 A 9/2000 Lee et al.
6,123,819 A 9/2000 Peeters
6,175,053 B1 1/2001 Tsubouchi
6,592,623 B1 7/2003 Bowlin et al.
6,815,427 B2 11/2004 Tsubouchi et al.
6,902,932 B2 6/2005 Altman et al.
6,951,053 B2 10/2005 Padilla et al.
7,041,797 B2 5/2006 Vollrath
7,057,023 B2 6/2006 Islam et al.
7,150,879 B1 12/2006 Lee et al.
7,166,570 B2 1/2007 Hunter et al.
7,241,736 B2 7/2007 Hunter et al.
7,285,637 B2 10/2007 Armato et al.
7,635,755 B2 12/2009 Kaplan et al.
7,662,409 B2 2/2010 Masters
7,674,882 B2 3/2010 Kaplan et al.
7,727,575 B2 6/2010 Kaplan et al.
7,842,780 B2 11/2010 Kaplan et al.
7,960,509 B2 6/2011 Kaplan et al.
8,071,722 B2 12/2011 Kaplan et al.
2002/0028243 A1 3/2002 Masters
2002/0155137 A1 10/2002 Lee et al.
2002/0155167 A1 10/2002 Lee et al.
2003/0007991 A1 1/2003 Masters
2003/0099630 A1 5/2003 DiBenedetto et al.
2003/0183978 A1 10/2003 Asakura
2004/0005363 A1 1/2004 Tsukada et al.
2004/0033212 A1 2/2004 Thomson et al.
2004/0078090 A1 4/2004 Binette et al.
2004/0258729 A1* 12/2004 Czernuszka et al. ......... 424/426
2004/0266992 A1 12/2004 Migliaresi et al.
2005/0119732 A1 6/2005 Furuzono et al.
2005/0147690 A1 7/2005 Masters et al.
2005/0260706 A1 11/2005 Kaplan et al.
2005/0267560 A1 12/2005 Bates
2005/0277577 A1* 12/2005 Hunter et al. .................... 514/2
2005/0287084 A1* 12/2005 Ibrahim et al. ................. 424/49
2006/0067969 A1 3/2006 Lu et al.
2006/0159837 A1* 7/2006 Kaplan et al. ................. 427/2.1
2006/0240064 A9 10/2006 Hunter et al.
2006/0273279 A1 12/2006 Kaplan et al.
2007/0150059 A1 6/2007 Ruberte et al.
2007/0179618 A1 8/2007 Trieu et al.
2007/0187862 A1 8/2007 Kaplan et al.
2007/0212730 A1 9/2007 Vepari et al.
2007/0255422 A1 11/2007 Wei et al.
2008/0085272 A1 4/2008 Kaplan et al.
2008/0293919 A1 11/2008 Kaplan et al.
2009/0048677 A1* 2/2009 McLeod et al. ........... 623/17.16
2009/0142385 A1 6/2009 Gross et al.
2009/0171467 A1 7/2009 Mann et al.
2009/0202614 A1 8/2009 Kaplan et al.
2009/0232963 A1 9/2009 Kaplan et al.
2009/0234026 A1 9/2009 Kaplan et al.
2009/0297588 A1 12/2009 Rheinnecker et al.
2010/0028451 A1 2/2010 Kaplan et al.
2010/0046902 A1 2/2010 Kaplan et al.
2010/0055438 A1 3/2010 Kaplan et al.
2010/0063404 A1 3/2010 Kaplan et al.
2010/0065784 A1 3/2010 Kaplan et al.
2010/0068740 A1 3/2010 Kaplan et al.
2010/0070068 A1 3/2010 Kaplan et al.
2010/0095827 A1 4/2010 Rheinnecker et al.
2010/0096763 A1 4/2010 Kaplan et al.
2010/0120116 A1 5/2010 Kaplan et al.
2010/0178304 A1 7/2010 Wang et al.
2010/0191328 A1 7/2010 Kaplan et al.
2010/0196447 A1 8/2010 Kaplan et al.
2010/0292338 A1 11/2010 Rheinnecker et al.
2011/0046686 A1 2/2011 Kaplan et al.
2011/0076384 A1 3/2011 Cannizzaro et al.
2011/0121485 A1 5/2011 Rheinnecker et al.
2011/0135697 A1 6/2011 Omenetto et al.
2011/0152214 A1 6/2011 Boison et al.
2011/0171239 A1 7/2011 Kaplan et al.
2012/0121820 A1 5/2012 Kaplan et al.
2012/0123519 A1 5/2012 Lovett et al.

FOREIGN PATENT DOCUMENTS

CN 1575188 A 2/2005
CN 1736492 2/2006
EP 1440088 7/2004
GB 1182153 2/1970
JP 55-139427 10/1980
JP 58-38449 8/1983
JP 60-142259 7/1985
JP 60-259677 12/1985
JP 01118544 11/1989
JP 1288269 11/1989
JP 04-263611 9/1992
JP H05-43600 A 2/1993
JP 06-346314 12/1994
JP 08-295697 11/1996
JP 10-36676 2/1998
JP 2000-273264 10/2000
JP 2003154001 A 5/2003
JP 2003192807 7/2003
JP 2004068161 3/2004
JP 2005510268 W * 4/2005
WO WO 9708315 A1 * 3/1997
WO 99/01089 1/1999
WO 01/36531 5/2001
WO 01/56626 8/2001
WO 02/072931 9/2002
WO 03/022909 3/2003
WO 03/035124 5/2003
WO 03/038033 5/2003
WO WO 03035124 A2 * 5/2003
WO 04/000915 12/2003
WO 2004/041845 5/2004
WO 2005/012606 2/2005
WO 2005012606 2/2005
WO 2005/123114 12/2005
WO WO-2007/020449 A2 2/2007
WO 2008/127405 10/2008
WO 2009/156226 12/2009
WO 2011/006133 1/2011

OTHER PUBLICATIONS

Li, C. et al., Biomaterials, 27(Iss. 16):3115-3124 (2006). "Electrospun silk-BMP-2 scaffolds for bone tissue engineering."

Meinel, L. et al., Bone Tissue Engineering Using Human Mesenchymal Stem Cells Effects of Scaffold Material and Medium Flow, Annals of Biomedical Engineering, 32(1):112-122 (2004).

Minoura, N. et al., Fine structure and oxygen permeability of silk fibroin membrane treated with methanol, Polymer 31:265-269 (1990).

Nazarov, R. et al., Porous 3-D Scaffolds from Regenerated Silk Fibroin, Biomacromolecules 5:718-726 (2004).

(56) References Cited

OTHER PUBLICATIONS

Tsukada, M. et al., Structural Changes of Silk Fibroin Membranes Induced by Immersion in Methanol Aqueous Solutions, Journal of Polymer Science: Part B: Polymer Physics, 32:961-968 (1994).
Li et al., European Cells and Materials, 14(1):76 (2007). "Porous silk/hydroxyapatite scaffolds for bone tissue engineering."
Lu et al., 2006 International Forum on Textile Science and Engineering for Doctoral Candidates, 2006. "A Hydroxyapatite Silk Fibroin Porous Composite Using Ultrasonic Vibration Method."
Agarwal et al., Journal of Applied Polymer Science, 63(3):401-410 (1997). "Effect of Moisture Absorption on the Thermal Properties of *Bombyx mori* Silk Fibroin Films."
Altman et al., Biomaterials, 24:401-416 (2003). "Silk-based biomaterials."
Ando et al, Reports on Progress in Polymer Physics in Japan, XXIII:775-778 (1980). "Piezoelectric and Related properties of Hydrated Silk Fibroin."
Asakura et al., Macromolecules, 17:1075-1081 (1984). NMR of silk fibroin 2. 13C NMR study of the chain dynamics and solution structure of *Bombyx mori* silk fibroin.
Asakura et al., Macromolecules, 18:1841-1845 (1985). "Conformational characterization of *B. mori* silk fibroin in the solid state by high-frequency 13C cross polarization-magic angle spinning NMR, X-ray diffraction and infrared spectroscopy."
Chen et al., J Appl Polymer Sci, 65:2257-2262 (1997). "pH sensitivity and ion sensitivity of hydrogels based on complex-forming chitosan/silk fibroin interpenetrating polymer network."
Chen et al., J Appl Polymer Sci, 73:975-980 (1999). "Separation of alcohol-water mixture by pervaporation through a novel natural polymer blend membrane-chitosan/silk fibroin blend membrane."
Chen et al., Proteins: Structure, Function, and Bioinformatics, 68:223-231 (2007). "Conformation transition kinetics of *Bombyx mori* silk protein."
Database WPI Week 198205, Derwent Publications Ltd., London, GB AN 1982-09092E & JP 56 166235 A Dec. 21, 1981. Abstract.
Demura et al., Biosensors, 4:361-372 (1989). "Immobilization of biocatalysts with *Bombyx mori* silk fibroin by several kinds of physical treatment and its application to glucose sensors."
Demura et al., J Membrane Science, 59:32-52 (1991). "Porous membrane of *Bombyx mori* silk fibroin: structure characterization, physical properties and application to glucose oxidase immobilization."
Derwent Record, Abstract of JP 08295697 A2 "Production of aqueous solution of silk fibroin at high concentration." Nov. 12, 1996.
Doshi et al. J Electrostatics, 35:151-160 (1995). "Electrospinning process and applications of electrospun fibers."
Freddi et al., J Appl Polymer Sci, 56:1537-1545 (1995). "Silk fibroin/cellulose blend films: preparation, structure, and physical properties."
Hijirida et al., Biophysical Journal, 71:3442-3447 (1996). "13C NMR of *Nephila clavipes* major ampullate silk gland."
Hinman et al., TIBTECH, 18:374-379 (2000). "Synthetic spider silk: a modular fiber."
Horan et al., Biomaterials, 26:3385-3393 (2005). "In vitro degradation of silk fibroin."
Hu et al., Biomacromolecules, 12:1686-1696 (2011). "Regulation of Silk Material Structure by Temperature-Controlled Water Vapor Annealing."
Huang et al., J Biomater Sci Polymer Edn, 12(9):979-993 (2001). "Engineered collagen-PEO nanofibers and fabrics."
Huang et al., Macromolecules, 33:2989-2997 (2000). "Generation of synthetic elastin-mimetic small diameter fibers and fiber networks."
Jin et al., Biomacromolecules, 3:1233-1239 (2002). "Electrospinning *Bombyx mori* silk with poly(ethylene oxide)."
Jin et al., Adv. Funct. Mater., 15:1241-1247 (2005). "Water-Stable Silk Films with Reduced β-Sheet Content."
Jin et al., Nature, 424:1057-1061 (2003). "Mechanism of silk processing in insects and spiders."
Kim et al., Biomacromolecules, 5:786-792 (2004). "Structure and Properties of Silk Hydrogels."
Kweon et al., J Appl Polymer Sci, 80:1848-1853 (2001). "Preparation of semi-interpenetrating polymer networks composed of silk fibroin and poly(ethylene glycol) macromer."
Lazaris, Science, 295:472-476 (2002). "Spider silk fibers spun from soluble recombinant silk produced in mammalian cells."
Li et al., Biomaterials, 27:3115-3124 (2006). "Electrospun Silk-BMP-2 scaffolds for bone tissue engineering."
Liang et al., J Appl Polymer Sci, 45:1937-1943 (1992). "Improvements of the physical properties of fibroin membranes with sodium alginate."
Lu et al., Acta Biomater. 6(4):1380-1387 (2010). "Water-Insoluble Silk Films with Silk I Structure."
Megeed et al., Pharmaceutical Research, 19(7):954-959 (2002). "Controlled release of plasmid DNA from a genetically engineered silk-elastinlike hydrogel."
Nazarov et al., Biomacromolecules, 5:718-726 (2004). "Porous 3-D Scaffolds from Regenerated Silk Fibroin."
Petrini et al., Journal of Materials Science: Materials in Medicine, 12:849-853 (2001). "Silk fibroin-polyurethane scaffolds for tissue engineering."
Reneker et al., Nanotechnology, 7:216-223 (1996). "Nanometre diameter fibres of polymer, produced by electrospinning."
Sawyer et al., JAMA, 191(9):740-742 (1965). "Dextran therapy in thrombophlebitis." Abstract.
Sofia et al., Journal of Biomedical Materials Research, 54(1):139-148 (2001). "Functionalized silk-based biomaterials for bone formation."
U.S. Appl. No. 60/906,509, filed Mar. 13, 2007 by Omenetto et al.
U.S. Appl. No. 61/224,618, filed Jul. 10, 2009 by Numata et al.
Wang et al., Langmuir, 21:11335-11341 (2005). "Biomaterial coatings by stepwise deposition of silk fibroin."
Wenk et al., Diss. Eth No. 18659 (2009). "Silk Fibroin As a Vehicle for Drug Delivery in Tissue Regeneration."
Yamada et al., Thin Solid Films, 440:208-216 (2003). "AFM observation of silk fibroin on mica substrates: morphologies reflecting the secondary structures."
Zhou et al., Chem Commun, 2518-2519 (2001). "Preparation of a novel core-shell nanostructured gold colloid-silk fibroin bioconjugate by the protein in situ redox technique at room temperature."
Liu et al., "Preparation and characterisation of nano-hydroxyapatite/silk fibroin porous scaffolds" J. Biomater. Sci. Polymer Edn. 19:325-338 (2008).
Nishiyama et al., "Application of silk fibroin to bone reconstruction material [in Japanese]" J. Oral Biosci., 2005, vol. 47, No Supplement, p. 168-169.
Wen, G. et al., "Study on Tissue Engineering Scaffolds of Silk Fibroin-Chitosan/nano-Hydroxyapatite Composite" Key Eng. Mater., 2007, vol. 330-332, No. 2, p. 971-974.
Japanese Patent Application No. 2010-546025; Notice of Reasons for Rejection dated Oct. 7, 2013 (and English translation).
Japanese Notice of Reasons for Rejections in Japanese Patent Application No. 2010-546025, mailed Apr. 9, 2014.
Computer Translation of JP 2004/068161 A, 40 pages (translated May 13, 2009).
Database WPI Week 199001, Thomson Scientific, London, GB; AN 1990-004589 & JP1288269, Abstract, 1 page (Nov. 20, 1989).
Database WPI Week 200640, Thomson Scientific, London, GB; AN 2006-383260 & CN1736492A, Abstract, 1 page (Feb. 22, 2006).
Extended European Search Report for EP09707377.9, 8 pages (Apr. 19, 2013).
Tsukada, M., et al., Structure and Compatibility of Poly(vinyl Alcohol)-Silk Fibroin (PVA/SF) Blend Films, Journal of Applied Polymer Science, Part B: Polymer Physics, 32: 243-248 (1994).
Written Opinion for PCT/US2009/033309, 5 pages (Aug. 18, 2009).
Altman, G.H. et al., Silk matrix for tissue engineered anterior cruciate ligaments, Biomaterials, 23:4131-4141 (2002).
Asakura, T. and Kaplan, D. Silk Production and Processing, Encyclopedia of Agricultural Science, 4:1-11 (1994).

(56) References Cited

OTHER PUBLICATIONS

Cappello, J. et al., In-situ self-assembling protein polymer gel systems for administration, delivery, and release of drugs, J. Control. Release., 53(1-3):105-17 (1998).
Caterson, et al., Three-dimensional cartilage formulation by bone marrow-derived cells seeded in polylactide/alginate amalgam, Biomed Mater Res, 57:394-403 (2001).
Chen, J. et al., Transport of pharmaceuticals through silk fibroin membrane, Polymer, 35(13):2853-2856 (1994).
Dinerman, A. A. et al., Solute Diffusion in genetically engineered silk-elastinlike protein polymer hydrogels, J. Control. Release, 82:277-287 (2002).
Foo, C. W. P. and Kaplan, D. L., Genetic engineering of fibrous proteins: spider dragline silk and collagen, Adv. Drug Deliver. Rev., 54:1131-1143 (2002).
Harris, L. D. Et al., Open pore biodegradable matrices formed with gas foaming, Journal of Biomedical Material Research, 42(3):396-402 (1998).
Hersel, U. et al., RGD modified polymers: biomaterials for stimulated cell adhesion and beyond, Biomaterials, 24:4385-415 (2003).
Holy, et al., Use of a biomimetic strategy to engineer bone, J Biomed Mater Res, 65A:447-453 (2003).
Hutmacher, Scaffolds in tissue engineering bone and cartilage, Biomaterials, 21:2529-2543 (2000).
Karp, et al., Fabrication of Precise Cylindrical Three-Dimensional Tissue Engineering Scaffolds for In Vitro and In Vivo Bone Engineering Applications, The Journal of Craniofacial Surgery, 14(3):317-323 (2003).
Lucas, F. et al., The silk fibroins, Advances in Protein Chemistry, 107-242 (1958).
Martin, et al., Selective differentiation of mammalian bone marrow stromal cells cultured on three-dimensional polymer foams, J Biomed Mater Res, 55:229-235 (2001).
Megeed, Z. et al., Genetically engineered silk-elastinlike protein polymers for controlled drug delivery, Adv. Drug Delivery Rev., 54:1075-1091 (2002).
Ohgushi, et al., Calcium Phosphate Block Ceramic With Bone Marrow Cells in a Rat Long Bone Defect, CRC Handbook of Bioactive Ceramics, vol. II:235-238 (1990).
Panilaitis, B. et al., Macrophage responses to silk, Biomaterials, 24:3079-3085 (2003).
Perez-Rigueiro, Silkworm Silk as an Engineering Material, J Appl Plym Sci, 70:2439-2447 (1998).
Petite, et al., Tissue-engineered bone regeneration, Nature Biotechnology, 18:959-963 (2000).
Schaffner P. And Dard, M.M., Structure and function of RGD peptides involved in bone biology, Cell Mol Life Sci., 60:119-32 (2003).
International Search Report for PCT/US2009/033309, 4 pages (Aug. 18, 2009).
Jia, X. et al., Natural biomaterials and the biomimetic engineering materials thereof, Chemical Industry Press, pp. 196-197 (2007). [Partial English Translation].

* cited by examiner

Silk cocoons and fibroin after sericin extraction

Silk solution in dialysis cassette

Dialysis cassettes in hypotonic solution

Freeze dried silk

Silk solution poured into smaller capsules

Silk plugs bathing in methanol

30% hydroxyapatite-silk mixture with dough-like consistency being packed into a small capsule in which it will polymerize Completed 30% HA mineralized silk material prototype samples in variety of geometries & sizes Steps for preparing ~3mm sections of silk fiber:
A.Winding silk around bracket, B. sericin extraction, C. slicing silk, D. drying Prototype of cylindrical 30% HA mineralized silk polymer with 2% raw fiber

3-DIMENSIONAL SILK HYDROXYAPATITE COMPOSITIONS

CROSS REFERENCE TO RELATED APPLICATIONS

This application is a 35 U.S.C. §371 National Phase Entry application of International Application No. PCT/US2009/033309, filed Feb. 6, 2009, which designates the United States, and which claims benefit of priority under 35 U.S.C. §119(e) of the U.S. provisional application No. 61/026,896 filed Feb. 7, 2008, and U.S. provisional application No. 61/085,569 filed Aug. 1, 2008, the contents of which are incorporated herein by reference in their entirety.

GOVERNMENT SUPPORT

This invention was made with Government support under Grant Nos. ED002520 and EB003210 awarded by the National Institutes of Health. The Government has certain rights in the invention.

FIELD OF THE INVENTION

The present invention relates to a mixture of silk fibroin and hydroxyapatite. The invention further relates to the repair and replacement of bone and teeth.

BACKGROUND

A major goal of tissue repair and regeneration is to develop a biological alternative in vitro for producing an implantable structure that serves as a support and speeds regenerative growth in vivo within a defect area.

In recent years biodegradable polymers such as poly (glycolic acid), poly (L-lactic acid) (PLLA) and their copolymers poly(L-lactic-co-glycolic acid) (PLGA) have been used as scaffold materials in studies of tissue formation. (Sofia et al. Journal of Biomedical Materials research 2001, 54, 139-148). Advantages of these polymers include their biocompatibility and degradability. However, PLGA can induce inflammation due to the acid degradation products that result during hydrolysis (Sofia et al. Journal of Biomedical Materials Research 2001, 54, 139-148). There are also processing difficulties with polyesters that can lead to inconsistent hydrolysis rates and tissue response profiles. Thus, there is a need for polymeric materials that have more controllable features such as hydrolysis rates, structure, and mechanical strength, while also being bioresorbable and biocompatible. Biological polymeric materials often demonstrate combinations of properties which are unable to be reproduced by synthetic polymeric materials. (Perez-Rigueiro et al. Science, 1998; 70: 2439-2447; Hutmacher D. Biomaterials 2000. 21, 2529-2543). Bone tissue is one example; scaffolds for bone tissue regeneration require high mechanical strength and porosity along with biodegradability and biocompatibility.

Several studies have shown that bone marrow stem cells (BMSCs) can differentiate along an osteogenic lineage and form three-dimensional bone-like tissue (Holy et al. J. Biomed. Mater. Res. (2003) 65A:447-453; Karp et al., J. Craniofacial Surgery 14(3): 317-323). However, there are important limitations. Some calcium phosphate scaffolds show limited ability to degrade (Ohgushi et al. 1992. In CRC Handbook of Bioactive Ceramics. T. Yamamuro, L. L. Hench, and J. Wilson, editors. Boca Raton, Fla.: CRC Press. 235-238), or degradation is too rapid (Petite et al. 2000. Nat. Biotechnol. 18:959-963.) Difficulties in matching mechanical properties to support desired function also remain an issue (Harris et al. J. Biomed. Mater. Res. 42:396-402).

Studies have also shown that BMSCs can differentiate along chondrogenic lineage and form three-dimensional cartilage-like tissue on biomaterial substrates, such as poly (lactic-co-glycolic acid) or poly-L-lactic acid (Caterson et al. 2001. J. Biomed. Mater. Res. 57:394-403; Martin et al. 2001. J. Biomed. Mater. Res. 55:229-235). However, the use of these scaffolds for cartilage formation manifests with the same limitations as observed with their use in bone engineering.

There exists a need for new biocompatible polymers, particularly polymers suitable for formation of scaffolds for mechanically robust applications such as bone or cartilage.

SUMMARY OF THE INVENTION

The search for new biomaterials in dentistry and medicine has expanded into natural materials such as protein polymers. Silkworm silk such as that processed from *Bombyx mori* is a candidate for applications in dentistry and medicine, ranging from restoration materials to tissue engineering scaffolds.

Described herein are methods and compositions comprising a mixture of silk polymer and hydroxyapatite. The methods described herein can be used to prepare a mixture of silk polymer and hydroxyapatite and further provide mixtures that can be molded into a desired shape. The methods and compositions described herein permit the formation of implantable structures, which can be implanted, for example, to facilitate bone healing or tooth structure or support.

In one aspect described herein, the inventors have developed an article of manufacture comprising a mixture of silk polymer and hydroxyapatite particles, wherein silk is formed into an insoluble state about hydroxyapatite particles. In this aspect and all other aspects described herein, an article of manufacture can be formed by mixing the silk polymer and hydroxyapatite particles prior to the formation of the silk insoluble state.

In one embodiment of this aspect and all other aspects described herein, silk polymer and hydroxyapatite particles are mixed together to form a substantially homogenous admixture.

In another embodiment of this aspect and all other aspects described herein, a mixture of silk polymer and hydroxyapatite particles can be solidified in a vessel of desired shape/size, such that the resulting article substantially retains the shape of a vessel in which it was formed.

In another embodiment of this aspect and all other aspects described herein, a mixture of silk polymer and hydroxyapatite particles can vary in composition at the discretion of one skilled in the art, such that the article comprises 0.1% to 90% hydroxyapatite by weight (and all compositions within the range of 0.1% to 90% hydroxyapatite).

In other embodiments of this aspect and all other aspects described herein, an article produced with a mixture of silk polymer and hydroxyapatite further comprises a bioactive agent. Alternatively, or in addition, the article can further comprise raw silk fiber.

Another aspect of the invention disclosed herein is the production of an implantable structure comprising a mixture of silk polymer and hydroxyapatite particles, wherein the silk polymer substantially surrounds the hydroxyapatite particles. In one embodiment, the implantable structure is formed from a substantially homogeneous mixture of silk polymer and hydroxyapatite particles.

In another embodiment of this aspect and all other aspects described herein, a mixture of silk polymer and hydroxyapatite particles can be solidified in a vessel of desired shape/size, such that a resulting structure substantially retains the shape of a vessel in which it was formed.

In another embodiment of this aspect and all other aspects described herein, a structure of silk and hydroxyapatite provides a temporary support that is bioresorbed after implantation, or alternatively, becomes integrated into bone following implantation.

Another aspect described herein, is a method for manufacture of an implantable structure, which comprises mixing a solution of silk polymer with hydroxyapatite particles and inducing the silk polymer to form an insoluble state, such that the silk polymer is formed into an insoluble state around the hydroxyapatite particles.

Also disclosed herein are kits for the production of implantable structures, the kits or systems comprising (a) lyophilized silk polymer or silk polymer and (b) hydroxyapatite particles (c) packaging materials therefore. In one embodiment, the kit or system further comprises a solvent, e.g., HFIP. In another embodiment, the system further comprises a vessel for the formation of silk polymer into an insoluble state.

Also described herein is a method for repairing or strengthening a bone in an individual, the method comprising the steps of: (a) mixing a solution of silk polymer with hydroxyapatite particles to form a paste composition, (b) applying the paste composition to a region of a bone in need of repair or reinforcement in an individual having a bone injury or a defect; and (c) forming the silk polymer in the applied paste composition into an insoluble state; wherein the applied composition comprising silk polymer in an insoluble state provides a scaffold for replacement by bone tissue.

Definitions

As used herein, the term "silk polymer" or "silk fibroin" includes silkworm fibroin and insect or spider silk protein (Lucas et al., Adv. Protein Chem 13: 107-242 (1958)). Preferably, fibroin is obtained from a solution containing a dissolved silkworm silk or spider silk. Generally, silk polymer of silk fibroin has been treated to substantially remove sericin. The silkworm silk protein is obtained, for example, from *Bombyx mori*, and the spider silk is obtained, for example, from *Nephila clavipes*. In the alternative, silk proteins suitable for use in the present invention can be obtained from a solution containing a genetically engineered silk, such as from bacteria, yeast, mammalian cells, transgenic animals or transgenic plants. See, for example, WO 97/08315 and U.S. Pat. No. 5,245,012. As used herein, the term "raw silk" or "raw silk fiber" refers to silk fiber that has not been treated to remove sericin, and thus encompasses, for example, silk fibers taken directly from a cocoon.

As used herein the term "insoluble state" when used in reference to a silk polymer refers to the formation of or state of being in a substantially amorphous, primarily β-sheet conformation. The term 'formed into an insoluble state' is not intended to reflect polymerization of silk monomers into a silk polymer. Rather, it is intended to reflect the conversion of soluble silk polymer to a water insoluble state. As used herein silk polymer is in an 'insoluble state' if it can be pelleted by centrifugation or if it cannot be dissolved by immersion in or rinsing with water at 37° C. or less.

As used herein, the term "about said hydroxyapatite particles" refers to the formation of a substantially homogeneous mixture of silk polymer and hydroxyapatite particles, such that the solidification or formation of the silk into an insoluble state occurs in the same vessel and as substantially one unit. Thus, the term "about said hydroxyapatite particles" excludes, for example, the secondary deposition of hydroxyapatite particles onto pre-formed insoluble silk polymers. The term "substantially homogeneous" means that the silk polymer and hydroxyapatite particles are combined together to form e.g., a paste, wherein the silk and hydroxyapatite are interdispersed well as a mixture.

As used herein, the term "bioresorbed" or "bioresorption" refers to infiltration of endogenous tissue or cells into an implanted structure, which permits integration of the implantable structure and tissues, where one or more components of the implanted structure is replaced by new tissue.

As used herein the term "comprising" or "comprises" is used to refer to compositions, methods, and respective component(s) thereof, that are essential to the invention, yet open to the inclusion of unspecified elements, whether essential or not.

As used herein the term "consisting essentially of" describes the incorporation of other elements that can be included in the description of the composition, method or respective component thereof and are limited to those that do not materially affect the basic and novel characteristic(s) of the invention.

The term "consisting of" refers to inventions, compositions, methods, and respective components thereof as described herein, which are intended to be exclusive of any element not deemed an essential element to the component, composition or method.

Figure 1:
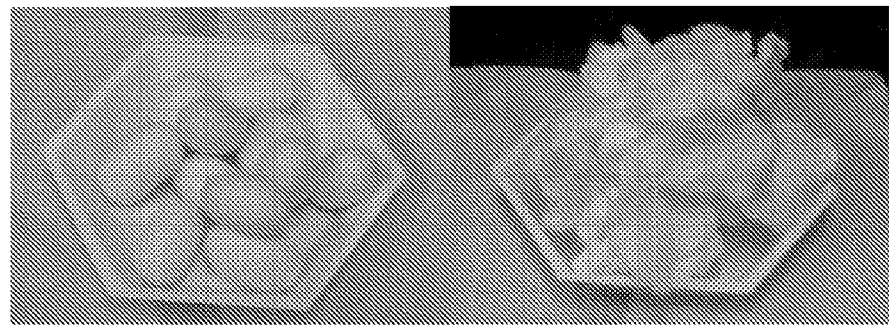
FIG. 1 shows an example of silk cocoons before and after sericin extraction.

Table 1 shows the compressive modulus values of non-mineralized silk polymer, mineralized silk biopolymer and commercially available dental composite resin restorative material.

Table 2 shows the shear bond strength of composite and mineralized silk polymer bonded to dentin.

DETAILED DESCRIPTION OF THE INVENTION

Isolation of Silk Polymer

Silk is a well described natural fiber produced by the silkworm, *Bombyx mori*, which has been used traditionally in the form of threads in textiles for thousands of years. This silk contains a fibrous protein termed fibroin (both heavy and light chains) that form the thread core, and glue-like proteins termed sericin that surround the fibroin fibers to cement them together. The fibroin is a highly insoluble protein containing up to 90% of the amino acids glycine, alanine and serine leading to β-pleated sheet formation in the fibers (Asakura, et al., Encyclopedia of Agricultural Science, Arntzen, C. J., Ritter, E. M. Eds.; Academic Press: New York, N.Y., 1994; Vol. 4, pp 1-11).

Silk provides an important set of material options for biomaterials and tissue engineering because of the impressive mechanical properties, biocompatibility and biodegradability (Altman, G. H., et al., Biomaterials 2003, 24, 401-416; Cappello, J., et al., J. Control. Release 1998, 53, 105-117; Foo, C. W. P., et al., Adv. Drug Deliver. Rev. 2002, 54, 1131-1143; Dinerman, A. A., et al., J. Control. Release 2002, 82, 277-287; Megeed, Z., et al., Adv. Drug Deliver. Rev. 2002, 54, 1075-1091; Petrini, P., et al., J. Mater. Sci-Mater. M. 2001, 12, 849-853; Altman, G. H., et al., Biomaterials 2002, 23, 4131-4141; Panilaitis, B., et al., Biomaterials 2003, 24, 3079-3085). The unique mechanical properties of reprocessed silk such as fibroin and its biocompatibility make the silk fibers especially attractive for use in biotechnological materials and medical applications. For example, 3-dimensional porous silk scaffolds have been described for use in tissue engineering (Meinel et al., Ann. Biomed. Eng. 2004 January; 32(1):112-22; Nazarov, R., et al., Biomacromolecules (2004), 5, 718-726). Further, regenerated silk fibroin films have been explored as oxygen- and drug-permeable membranes, supports for enzyme immobilization, and substrates for cell culture (Minoura, N., et al., Polymer 1990, 31, 265-269; Chen, J., et al., Minoura, N., Tanioka, A. 1994, 35, 2853-2856; Tsukada, M., et al., Polym. Sci. Part B Polym. Physics 1994, 32, 961-968). In addition, silk hydrogels have found numerous applications in tissue engineering, as well as in drug delivery (Megeed et al., Pharm. Res. 2002 July; 19(7):954-9; Dinerman et al., J. Control. Release. 2002 Aug. 21; 82(2-3):277-87).

Described herein are methods and compositions for the preparation of implantable structures comprising silk and hydroxyapatite. In these structures, silk polymer is formed into an insoluble state about hydroxyapatite particles. The structures find use as implants to support bone or tooth repair, or for example to deliver one or more bioactive agents to a site of implantation. Methods, materials, and considerations for the practice of the invention described herein are described in the following. The silk fibroin solution to be concentrated can be prepared by any method known to one skilled in the art.

One approach uses sericin extraction by boiling silkworm cocoons in $Na_2CO_3$, followed by solubilization in lithium bromide (LiBr), lyophilization and re-dissolution in the organic solvent hexafluoroisopopanol (HFIP) prior to addition to a vessel for creation of an article of manufacture is described in the Examples.

Alternatively, it can be advantageous to avoid the use of organic solvents. Such solvents can pose biocompatibility problems when the processed materials are exposed to cells in vitro, or in vivo. Further, where it is desired to include a bioactive agent e.g., a growth factor or other bioactive molecule in the structures to be implanted, it can be advantageous to use an all-aqueous approach in order to maintain the activity of the agent.

Organic solvents can also change the properties of fibroin material. For example, the immersion of silk fibroin films in organic solvents such as methanol causes dehydration of the hydrated or swollen structure, leading to crystallization and thus, loss of solubility in water. Further, with respect to tissue engineering scaffolds, the use of organic solvents can render the silk material to be less degradable.

An all-aqueous approach for preparing silk to be used in preparing mineralized silk preparations as described herein, is described, for example, in U.S. 20070187862, which is incorporated herein by reference.

Minerals

Minerals for use in the methods described herein, can include any biocompatible mineral that one desires to use. A preferred mineral is hydroxyapatite, which has well-known characteristics with respect to its compatibility with bone. Hydroxyapatite particles of varying size can be used to synthesize an implantable structure, and are available in nanocrystal, powder, granules and blocks from commercial sources such as Berkeley Advanced Biomaterials (Berkeley, Calif.). The size of hydroxyapatite particles can vary widely depending on the material properties desired following silk insolubilization. The particles of hydroxyapatite can be, for example, nanoparticles or alternatively, can be very large, for example, 500 μm and up to millimeter sizes. The size of particle used will alter the properties of the article of manufacture, such as compressive modulus, shear bond strength and porosity. Methods for use of a variety of hydroxyapatite particle sizes are contemplated herein.

Combination of Silk Polymer and Hydroxyapatite Particles

Described herein are methods relating to the production of an article or an implantable structure comprising a mixture of silk polymer and hydroxyapatite particles. The silk polymer is isolated and treated as described herein above. Silk polymer and hydroxyapatite particles are mixed into a substantially homogenous mixture, e.g., a paste, and the silk polymer is formed into an insoluble state in the presence of, and preferably surrounding, the hydroxyapatite particles. The formation of a homogeneous mixture does not encompass dissolution of the hydroxyapatite particles, but rather the particles are inter-mixed with the dissolved silk to produce a paste-like substance. The insoluble structure produced can be used as an implantable structure.

The amount of hydroxyapatite particles can vary from 0.1% hydroxyapatite by weight to 90% hydroxyapatite by weight. Preferably, the hydroxyapatite particles are at least 1%, at least 2%, at least 5%, at least 10%, at least 20%, at least 30%, at least 40%, at least 50%, at least 60%, at least 70%, at least 80%, up to and including at least 90% by weight, or any percentage of hydroxyapatite within this range. For example, the hydroxyapatite particles can be within the range of 0.1% to 90%, 0.1% to 80%, 0.1% to 70%, 0.1% to 60%, 0.1% to 50%, 0.1% to 40%, 0.1% to 30%, 0.1% to 20%, 0.1% to 10%, 0.1% to 5%, 0.1% to 1%, 90% to 80%, 90% to 70%, 90% to 60%, 90% to 50%, 90% to 40%, 90% to 30%, 90% to 20%, 90% to 10%, 90% to 5%, 90% to 2%, 90% to 1%, 90% to 0.1%, 10% to 50%, 15% to 45%, 20% to 40%, 30% to 70%, 30% to 60%, 30% to 50%, 30% to 40%, 10% to 30%, 15% to 30%, or 20% to 30%.

Formation of Silk into an Insoluble State

In general, regenerated silk fibroin is soluble in water and requires immersion in an alcohol or other suitable agent to obtain an insoluble, amorphous composition comprising primarily silk polymer as a β-sheet structure (Sofia et al. Journal of Biomedical Materials Research 2001, 54, 139-148). Therefore, prior to submersion into aqueous solutions the silk structures are first soaked in a β-sheet structure inducing agent, such as alcohol to induce the phase transition to β-sheet structure. The type of a β-sheet structure inducing agent can be selected to generate structures with different properties. For example, when methanol and propanol are used to induce β-sheet structure, the resulting structures are stronger but more brittle and therefore suitable in bone regeneration. Various methods of silk insolubilization including insolubilization that does not rely upon organic solvents or alcohol are contemplated herein and can be adapted based on the characteristics required for the article or structure described herein. U.S. 20070187862 describes an all-aqueous approach for the preparation of insoluble silk structures from solubilized silk fibroin.

Vessels

The silk polymer described herein can be formed into an insoluble state in any vessel, provided that the silk can be removed from the vessel. A vessel is any container that the silk mixture can be poured or packed into, which comprises a cavity having the shape of the desired structure following formation of the silk into an insoluble state. Thus, upon removal of the vessel, the silk-hydroxyapatite structure substantially retains the shape of the vessel cavity. A vessel can be larger in volume than the volume of the desired structure, since, for example the formation of silk into an insoluble state can be accompanied by a shrinking of a silk-hydroxyapatite mixture. In addition, vessels around which the silk mixture can be formed into an insoluble state are also contemplated herein, such that solidified silk retains the shape of the outer surface of a vessel.

A vessel can be composed of, for example, plastic, glass, ceramic or metal. In some embodiments it may be beneficial to utilize a vessel that is flexible to allow silk polymer removal without structural damage to the article produced. Vessels used in the methods described herein can vary widely at the discretion of one skilled in the art. In addition, the choice of vessel can easily be modified to fit a specific need.

It should be understood that implantable structure as described herein can alternatively, or in addition, be milled from a block or other structure to produce the final implantable structure. Thus, formation in a vessel of the desired shape can be used, or a given shape can be milled or carved by one of skill in the art to produce the desired shape.

Implantable Structures

An "implantable structure" is generally any structure that upon implantation does not generate an immune response in the host organism. Thus, an implantable structure should not for example, be or contain an irritant, or contain LPS etc. In addition, in some instances, it is preferred that an implantable structure should permit or not prohibit cell infiltration, blood vessel growth or other properties that would inhibit bioresorption or integration of the structure into tissue. For such instances, for example, it is important that the structure is not simply a solid 3-dimensional form but comprises or develops some porosity such that cells, etc., can gain access during the resorption process (that is, unless the lack of bioresorption is desired). While it is generally preferred that an implantable structure does not raise or provoke an immune response (e.g., inflammation or the raising of antibodies against a component of an implant), in some cases it can be beneficial for the structure to induce an immune-response (e.g., generation of antibodies against a specific antigen) or to prevent integration into tissue. Such aspects are also contemplated within the methods described herein.

An implantable structure can be applied to a wide variety of uses, however it is preferred that an implantable structure, as described herein, is implanted for the repair or support of bone or tooth structures. Implantable silk structures can be used e.g., to give temporary support for teeth, for broken bones, for fragile/weak bones, or to speed healing of bone fractures, breaks, loss of calcification, etc. Structures or articles of manufacture described herein can also be used to deliver a bioactive agent, either as a primary use or secondary to repair or support of a tissue. Bioactive agents useful in such embodiments are described herein below.

In general, the length of the tissue regenerative growth period will depend on the particular tissue being implanted with a silk structure. The growth period can be continued until the new tissue has attained desired properties, e.g., until the regenerating tissue has reached a particular thickness, size, strength, composition of proteinaceous components, and/or a particular cell density. Methods for assessing these parameters are known to those skilled in the art. The implantable structure should reabsorb at a rate that does not exceed the growth period of the tissue. Thus, the structure should remain substantially intact until sufficient infiltration of surrounding tissue occurs (as detected by methods known in the art) and the implantable structure is no longer necessary for tissue strength or structure (e.g., bone density). Such agents can provide prophylactic or therapeutic benefit either in situ, e.g., through promotion of desired biological processes, or, e.g., by leaching out of the structure after implantation.

Bioactive Agents

In one preferred embodiment, additives such as pharmaceutical/therapeutic agents, or biologically active agents, are incorporated into a silk-hydroxyapatite mixture. For example, growth factors, pharmaceuticals, or biological components can be incorporated into the mixture during formation of the implantable structure.

The variety of different pharmaceutical/therapeutic agents that can be used in conjunction with the methods described herein is wide and includes, but is not limited to small molecules, proteins, antibodies, peptides and nucleic acids. In general, bioactive agents which can be administered via the invention include, without limitation: anti-infectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β-III), vascular endothelial growth factor (VEGF)); anti-angiogenic proteins such as endostatin, and other naturally derived or genetically engineered proteins, polysaccharides, glycoproteins, or lipoproteins. Growth factors important for, e.g., bone growth, are described in "The Cellular and Molecular Basis of Bone Formation and Repair" by Vicki Rosen and R. Scott Thies, published by R. G. Landes Company, incorporated herein by reference. Additionally, the mixtures described herein can be used to deliver any type of molecular compound, such as pharmacological materials, vitamins, sedatives, steroids, hypnotics, antibiotics, chemotherapeutic agents, prostaglandins, and radiopharmaceuticals. The silk hydroxyapatite structures described herein are suitable for delivery of the above materials and others including but not limited to proteins, peptides, nucleotides, carbohydrates, simple sugars, cells, genes, anti-thrombotics, anti-metabolics, growth factor inhibitor, growth promoters, anticoagulants, antimitotics, fibrinolytics, anti-inflammatory steroids, and monoclonal antibodies.

While the articles of manufacture themselves can be thought of, in some aspects, as a carrier for delivery of a bioactive agent, the bioactive agents/therapeutics/pharmaceuticals of the article of manufacture described herein can be formulated by mixing with a pharmaceutically acceptable carrier. Any pharmaceutical carrier can be used that does not dissolve or otherwise interfere with the solidified silk/hydroxyapatite structure. The bioactive or therapeutic agents can be added to the silk-hydroxyapatite mixtures as a liquid, a finely divided solid, or any other appropriate physical form. Alternatively, a bioactive agent can be added to a pre-formed silk-hydroxyapatite structure as described herein by immersing the structure in a solution comprising the bioactive agent. That is, the agent need not necessarily be present when the silk-hydroxyapatite structure is formed.

Examples of other biologically active agents suitable for use in the methods described herein include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard 2003 Cell Mol. Life. Sci. January; 60(1):119-32; Hersel U. et al. 2003 Biomaterials November; 24(24):4385-415); biologically active ligands; and substances that enhance or exclude particular varieties of cellular or tissue ingrowth. Such additives are particularly useful in tissue engineering applications where, for example, structures are engineered in vitro to include cells that impart a beneficial characteristic on the structure to be implanted. For example, the steps of cellular population of a 3-dimensional silk-hydroxyapatite scaffold matrix preferably are conducted in the presence of growth factors effective to promote proliferation of the cultured cells employed to populate the matrix. Agents that promote proliferation will be dependent on the cell type employed. For example, when fibroblast cells are employed, a growth factor for use herein may be fibroblast growth factor (FGF), most preferably basic fibroblast growth factor (bFGF) (Human Recombinant bFGF, UPSTATE Biotechnology, Inc.). Other examples of additive agents that enhance proliferation or differentiation include, but are not limited to, osteoinductive substances, such as bone morphogenic proteins (BMP); cytokines, growth factors such as epidermal growth factor (EGF), platelet-derived growth factor (PDGF), insulin-like growth factor (IGF-I and II), TGF-$\alpha$ and the like. Of course, such additive agents can be used in situations in which a host's cells are encouraged to infiltrate and/or replace an implanted structure in vivo.

Implantable structures can be used to deliver therapeutic agents to cells and tissues. The ability to incorporate, for example pharmaceutical agents, growth factors and other biological regulators, enzymes or possibly even cells in the structure described herein provides for stabilization of these components for long term release and stability, as well as better control of activity and release.

Other reagents, necessary or indicated for assisting the stability or activity of a bioactive agent can also be included in the mixtures used to create mineralized silk structures with bioactive agents as described herein. Thus, necessary buffers, salts or co-factors can be added as necessary.

Compressive Structures and Compressive Modulus Testing

Compressive modulus testing is known to, and can be performed by, one of skill in the art. For example, compressive modulus testing can be performed with an Instron® 3366 tester using a 10kN load cell. In an approach generally applicable to the testing of structures prepared as described herein, one day prior to testing, samples are soaked in 0.9% NaCl solution. Testing parameters are modified from ASTM Standard ASTM D695: Standard Test Method for Compressive Properties of Rigid Plastics (Volumes 03.01, 444-476 (2006); and 08.01, 78-85 (2006), which are incorporated herein by reference. A crosshead extension rate of 1 mm/min can be used with load, and displacement can be recorded at a sampling rate of 200 samples/min. The compressive modulus for the silkworm silk material is calculated using e.g., BlueHill® 1.9 Materials Testing Software using a segment modulus method that applies a least squares fit to the recorded data points between two load boundaries. The compressive modulus for composite material is calculated using stress-strain data recorded in a load range of 100N and 300N, as well as a 2500N and 4500N range. These ranges of loads are judged to be within the linear portions of the load deformation curve for each material.

Shear Bond Stress Testing

The shear bond stress test is a measure of the strength at which a silk-hydroxyapatite structure remains bonded to dentin under a certain shear.

First a silk-hydroxyapatite structure is prepared for testing and comparison to a similarly prepared composite of known shear bond strength. One method for preparing a silk-hydroxyapatite structure is as follows. In one embodiment, human teeth are extracted and set in acrylic. The teeth are trimmed to expose flat dentin surfaces, and polished wet with 240 grit sandpaper. A cylindrical mineralized silk biopolymer structure is prepared with appropriate dimensions for testing (e.g., ~6.5 mm diameter, ~4-6 mm height). The silk bonding surfaces are etched with 9.5% hydrofluoric acid and then cemented to dentin surfaces using resin cement (Variolink II, Ivoclar Vivadent) under an appropriate bonding pressure level (e.g., ~500 g+/−100 g). As a control, bonded composite-resin cylinders of similar dimensions can be prepared and bonded to dentin for comparison with the silk-hydroxyapatite structures. Composite-resin (4 Seasons, Ivoclar Vivadent) can be loaded into a plastic straw, in order to fabricate uniform composite cylinders for bonding (~5.8 mm diameter, ~5 mm height). The resin composite cylinders are bonded onto dentin surfaces using 5th generation single-component adhesive (Excite, Ivoclar Vivadent) and light-cured for 20s. Bonded specimens can be stored in 37° C. water for 24 hrs.

Shear bond strength can be obtained with an Instron 4202 at crosshead speed of 0.5 mm/min. The resulting strength of a silk-hydroxyapatite structure can then be compared to a composite of known strength or the strength of a silk structure lacking hydroxyapatite.

In Vivo Structure Formation

In addition to implanting a pre-formed structure, it is also contemplated herein that the structure can applied in a paste form and cured into an insoluble state in vivo. This method of administration is especially useful for tailoring the shape and size of the structure directly to the site of injury and is easily illustrated, for example, by bone repair. A portion of a bone can effectively be replaced or strengthened by the application of a silk-hydroxyapatite mixture directly to the region of disease or injury (i.e., defect site) and then formation of the mixture into an insoluble state. The bone can begin to repair itself and the implanted structure degrades over time to be replaced by the individual's own bone. Thus, there is no need for a further procedure to remove the silk structure. One major advantage of this mode of administration is that the shape of the implant can be molded into place at the site to be repaired and does not need to be designed and formed outside of the defect site.

The basic steps for in vivo structure formation include forming the silk-hydroxyapatite into an admixture, placing the admixture into a site requiring repair, and then forming the admixture into an insoluble state at the repair site (also referred to herein as "curing").

In order to minimize damage to tissues surrounding the site of repair, it is essential that an all aqueous approach be used to form the silk paste. In one embodiment, the silk solution (in water) containing the hydroxyapatite particles is prepared in a concentration gel or slurry. This system can either be injected into a defect site, or molded into a putty-like consistency and placed within the defect. The materials will harden during application and over time as the silk undergoes stabilization via beta sheet formation. Formation of the beta sheet occurs due to the shear stress imposed during injection or molding of the putty, due to local dehydration in the wound side, or a combination of these two effects.

Curing of the silk-hydroxyapatite paste into an insoluble state can also be achieved by preheating the mixture and then cooling prior to placement in the body. In addition, physiologically neutral accelerants such as glycerol can be used. In one embodiment, the silk-hydroxyapatite mixture is sonicated prior to placing it within the defect.

It is understood that the foregoing detailed description and the following examples are illustrative only and are not to be taken as limitations upon the scope of the invention. Various changes and modifications to the disclosed embodiments, which will be apparent to those skilled in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents. The present invention may be as defined in any one of the following numbered paragraphs.

1. An article of manufacture comprising a mixture of silk polymer and hydroxyapatite particles, wherein the silk is formed into an insoluble state about the hydroxyapatite particles.
2. An article of manufacture comprising a mixture of silk polymer and hydroxyapatite particles, wherein the silk is formed into an insoluble state in the presence of the hydroxyapatite particles.
3. The article of manufacture of paragraph 1 or 2, wherein the silk polymer and the hydroxyapatite particles are in substantially homogeneous admixture.
4. The article of manufacture of paragraph 1, 2 or 3, wherein the article substantially retains the shape of the vessel in which it was formed.
5. The article of manufacture of any one of paragraphs 1-4, wherein the article comprises 0.1 to about 90% hydroxyapatite by weight.
6. The article of manufacture of any one of the preceding paragraphs, which further comprises a bioactive agent.
7. The article of manufacture of any one of the preceding paragraphs, which further comprises raw silk fiber.
8. An implantable structure comprising a mixture of silk polymer and hydroxyapatite particles, wherein the silk polymer substantially surrounds the hydroxyapatite particles.
9. The structure of paragraph 8, wherein the silk polymer and the hydroxyapatite particles are in substantially homogeneous admixture.
10. The structure of paragraph 8 or 9, wherein the structure substantially retains the shape of the vessel in which it was formed.
11. The implantable structure of paragraph 8, 9, or 10, which is bioresorbed after implantation.
12. The implantable structure of any one of paragraphs 8-11, which becomes integrated into bone following implantation.
13. A method for manufacture of an implantable structure, the method comprising mixing a solution of silk polymer with hydroxyapatite particles and inducing the silk polymer to form an insoluble state, such that the silk polymer is formed into an insoluble state around the hydroxyapatite particles.
14. The method of paragraph 13, wherein the silk polymer and the hydroxyapatite particles are in substantially homogeneous admixture.
15. The method of paragraph 13 or 14, wherein the implantable structure comprises 0.1 to about 90% hydroxyapatite by weight.
16. The method of paragraph 13, 14, or 15, wherein the implantable structure further comprises a bioactive agent.
17. The method of any one of paragraphs 13-16, wherein the implantable structure further comprises raw silk fiber.
18. The method of any one of the preceding paragraphs, wherein the implantable structure substantially retains the shape of the vessel in which it was formed.
19. The method of any one of the preceding paragraphs, wherein the implantable structure is bioresorbed after implantation.
20. The method of any one of the preceding paragraphs, wherein the implantable structure becomes integrated into bone following implantation.
21. A kit for production of the implantable structures, the kit comprising:
    (a) lyophilized silk polymer,
    (b) hydroxyapatite particles, and
    (c) packaging materials therefore.
22. The kit of paragraph 21, the kit further comprising HFIP solvent.
23. The kit of paragraph 21 or 22, the kit further comprising a vessel for formation of silk polymer into an insoluble state.
24. A method for repairing or strengthening a bone in an individual, the method comprising the steps of:
    (a) mixing a solution of silk polymer with hydroxyapatite particles to form a paste composition, (b) applying the paste composition to a region of a bone in need of repair or reinforcement in an individual having a bone injury or a defect; and (c) forming the silk polymer in the applied paste composition into an insoluble state;

wherein the applied composition comprising silk polymer in an insoluble state provides a scaffold for replacement by bone tissue.

EXAMPLES

Example 1

One Embodiment of the Methodology Used to Make Silk/Hydroxyapatite Articles and Implantable Structures A. Extraction & Rinsing of Raw Silk Dried cocoons were cut open and the silkworm tissue extracted. In order to facilitate sericin extraction, the cocoons were chopped into several pieces and 5 g of silkworm cocoon tissue was boiled in 0.02M $NaCO_3$ solution for 30-45 minutes to extract the sericin from the silk cocoon. The silk was immersed loosely in the liquid while boiling to expose as much surface area as possible. The silk was removed from the solution, wrung and soaked in warm distilled water (1 L per 5 grams) in a beaker for 20 minutes with occasional stiffing. This step was repeated two more times and after the third wash, the silk was drained, wrung and laid out flat to dry under a hood for 12-18 hours. The mass of the dried silk was ~70-75% of the original mass of the sericin-free silk, as shown in FIG. 1.

B. Dissolving in Lithium-Bromide Solution

The silk was then dissolved in a 9.3M LiBr solution at a silk concentration of 20% weight/volume ratio of silk mass/LiBr. The silk was allowed to dissolve in a 60° C. chamber for 4 hours.

C. Dialysis of Silk Solution

Figure 2:
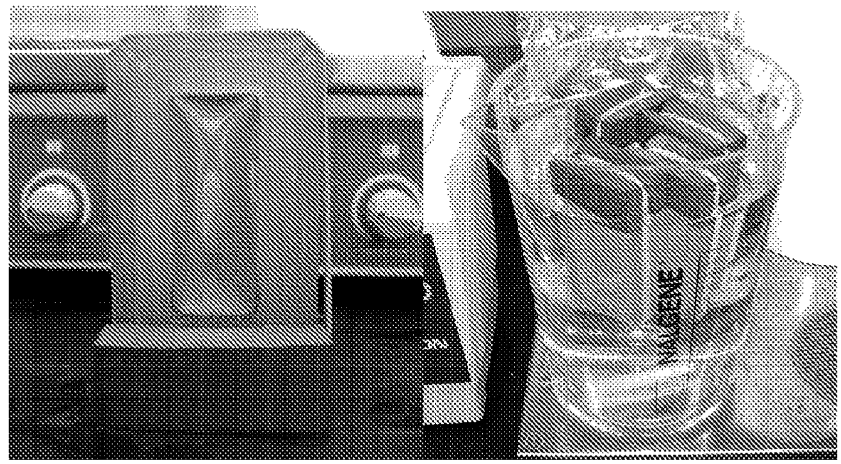
FIG. 2 shows a dialysis technique for a silk preparation method described herein. The left hand side of the figure shows the silk solution in a dialysis cassette, and the right hand side of the figure shows the dialysis of the cassettes in a hypotonic solution.

A syringe was used to transfer 12 mL aliquots of the dissolved silk solution into 12 mL dialysis cassettes. Each dialysis cassette with silk solution was dialyzed against 1 L of distilled water. For example, up to 4 cassettes may be included in one plastic 5 L capacity bucket and would require 4 L of water, as shown in FIG. 2. The distilled water was changed after 1 hour, 4 hours and then every 12 hours for the following 2 days to a total of 6 changes.

D. Centrifugation

Figure 3:
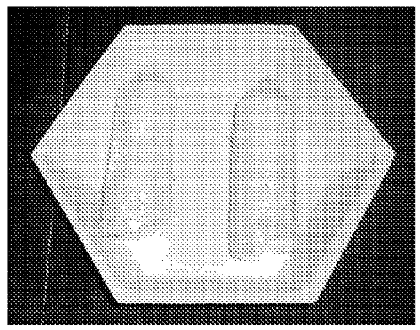
FIG. 3 shows a representative example of the freeze dried silk following lyophilization.
Figure 4:
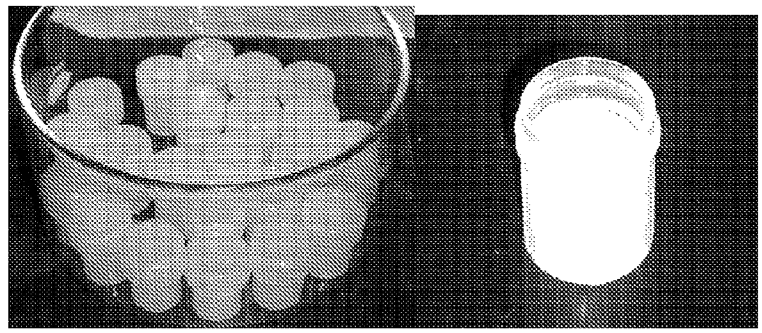
FIG. 4 shows an example of a vessel filled with silk solution and subsequent bathing of the silk solution in methanol to drive off the HFIP and allow the silk to solidify or form an insoluble state.

The silk solution was collected from a dialysis cassette using a syringe and transferred into a 45 mL Falcon™ centrifuge tube. The silk solution was refrigerated and then centrifuged @ 9,000 RPM for 30 minutes to remove any impurities/debris left over from the original cocoon (see FIG. 3). The centrifuge was allowed to slow to a gentle stop over a 20 minute period. The silk solution was transferred into new tubes, refrigerated and the centrifugation repeated a second time.

E. Freezing & Then Drying Silk

The top of the centrifuge tubes containing purified silk was removed and the tubes were placed in the freezer overnight. The frozen silk was lyophilized to produce pure freeze-dried silk. The silk in this form can be stored for several weeks at room temperature in a dry environment.

F. Dissolving the Silk in HFIP (hexa-fluoro-iso-propanol)

Figure 5:
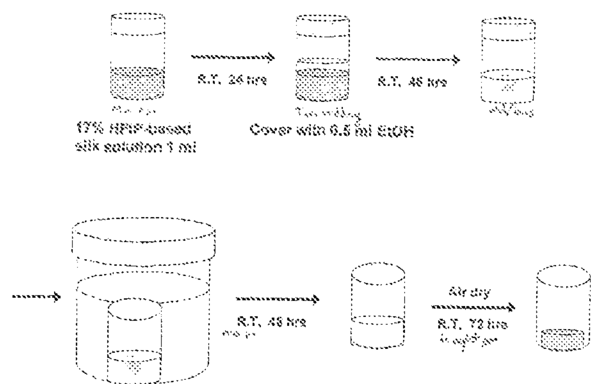
FIG. 5 shows a schematic depiction of one embodiment used herein to produce silk polymers and a photograph depicting exemplary silk blocks made using that method.
Figure 5:
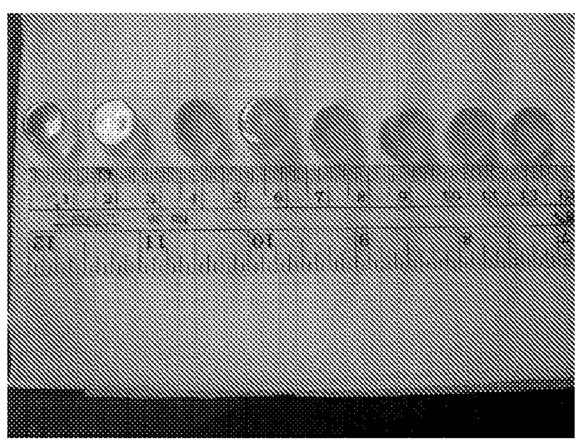

The freeze-dried silk was weighed and dissolved in 90% volume of HFIP required to yield a final concentration of 17% weight/volume of silk. The silk was allowed to dissolve for approximately 2 days before adding the final 10% of the HFIP. Following addition of the remainder of HFIP, the solution was left for approximately 4 hours to allow proper mixing of the solution. The silk dissolution process is depicted in FIG. 5.

G. Pouring Silk HFIP Solution into Repolymerization Capsule & HFIP Removal

Figure 6:
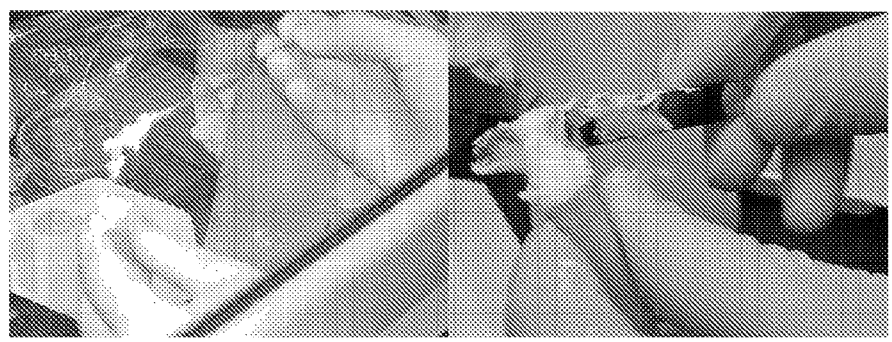
FIG. 6 shows an exemplary 30% hydroxyapatite-silk mixture and the packing of the mixture into an exemplary vessel.
Figure 7:
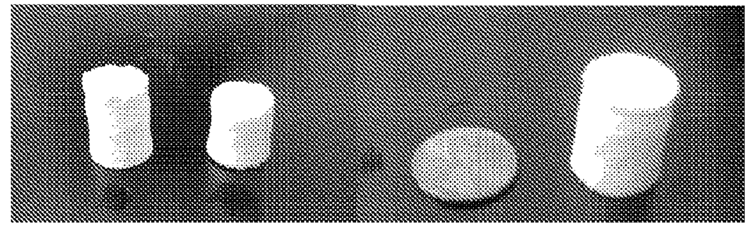
FIG. 7 shows photographs of some embodiments of silk polymer structures with various shapes and sizes.
Figure 7:
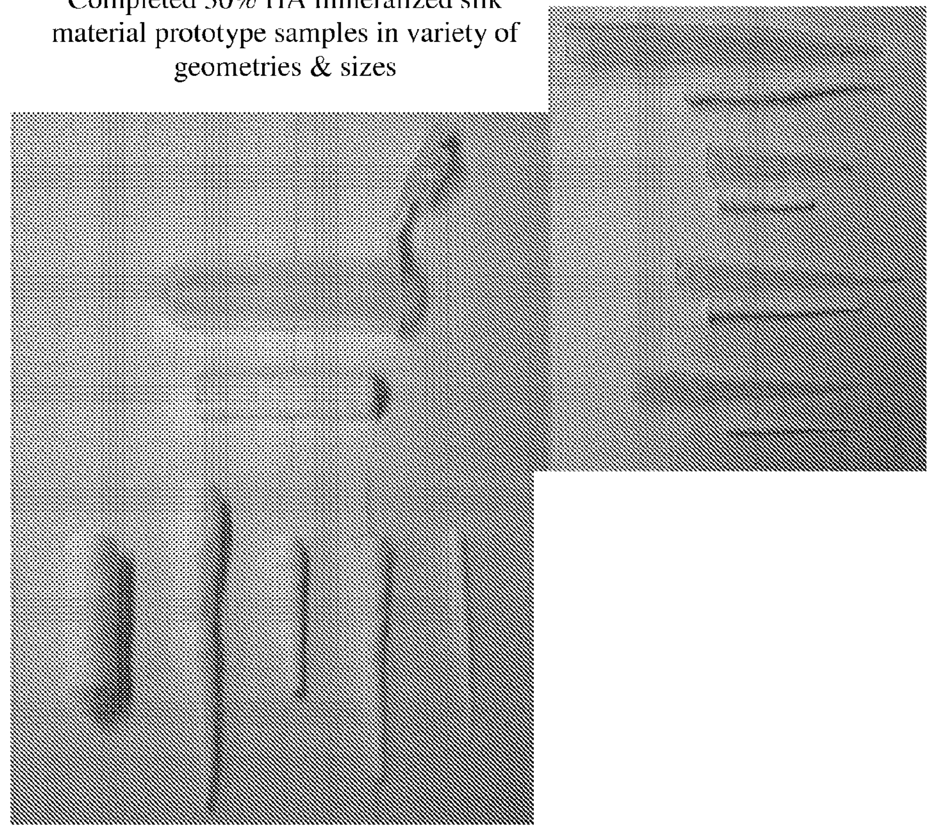

A syringe was used to transfer discrete volumes of the silk solution (following complete dissolution) into capsules for formation of insoluble silk structures. The capsules were chosen to seal tightly, but were of arbitrary shape such that the eventual silk blocks took the form of the capsule utilized (see FIG. 6).

After 24 h, methanol was added to silk capsules to accelerate the evaporation of the HFIP. The silk plugs shrank significantly in the presence of methanol as they solidified.

H. Mineralized Silkworm Silk Polymer Processing and Description

Inorganic mineral content was added to the silk solution, after it had been dissolved in HFIP, as a variation of the 17% silk polymer fabrication process. Prototypes of a mineral-loaded silk polymer were fabricated, e.g., to improve the mechanical properties of the material. The inorganic mineral content used was hydroxyapatite ($HA{=}Ca_{10}(PO_4)_6(OH)_2$).

Figure 8:
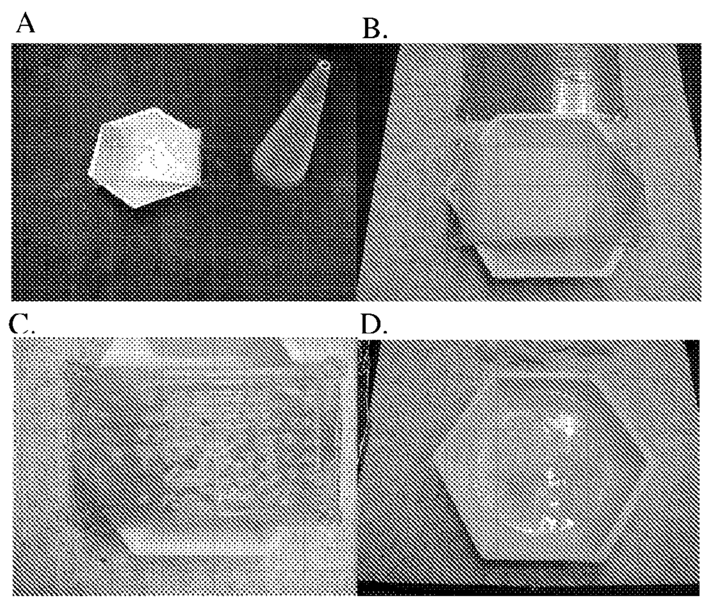
FIG. 8 depicts an exemplary method for producing silk fibers comprising the steps of (a) winding silk around a bracket, (b) sericin extraction, (c) slicing silk, and (d) drying silk.

Mineral loaded silk polymer materials with up to 30% HA were synthesized. Higher proportions can be prepared, if so desired, up to, e.g., 40%, 50%, 60%, 70%, 80%, 90% or more. Once the necessary amount of HA powder (to yield, in this instance, 30% by mass) was added into the silk-HFIP mixture, the resulting material had a dough-like consistency, as shown in FIG. 8. The viscosity of the mineral loaded silk material was higher than that of the pure silk solution, such that it was not feasible to aliquot with the use of a syringe. However, with sufficient pressure, the mineralized silk solution mixture could be poured into cavities of arbitrary geometry and size for the formation of insoluble silk-hydroxyapatite structures. For making prototypes of the mineralized silk material, the material was packed into items such as plastic pipette tips and cylindrical plastic capsules. It was discovered that a small opening at the distal end of the cavity being packed with material yielded better success allowing it to be filled with fewer voids.

Figure 9:
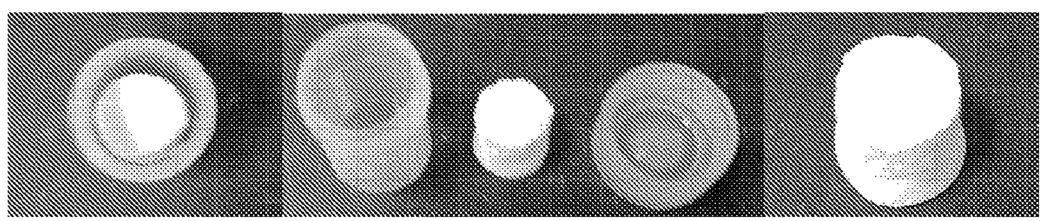
FIG. 9 shows an exemplary silk polymer block formed in the presence of non-dissolved silk fibers in a cylindrical vessel.

After being distributed into the capsule or mold an insoluble silk-hydroxyapatite structure, the mineralized silk material was processed to completion using the same steps as those followed for the non-mineralized silk material described herein. Silk polymer/hydroxyapatite structures with various shapes and sizes are shown in FIG. 9.

I. Mineralized Silkworm Silk Polymer with Integrated Raw Silk Fiber

Another variation of the silk polymer material in addition to added hydroxyapatite is to add non-dissolved silk fibers into the mixture to help structurally reinforce the silk polymer. This can be especially advantageous if, for example, the fibers are aligned parallel to the direction of compressive force being applied.

Figure 10:
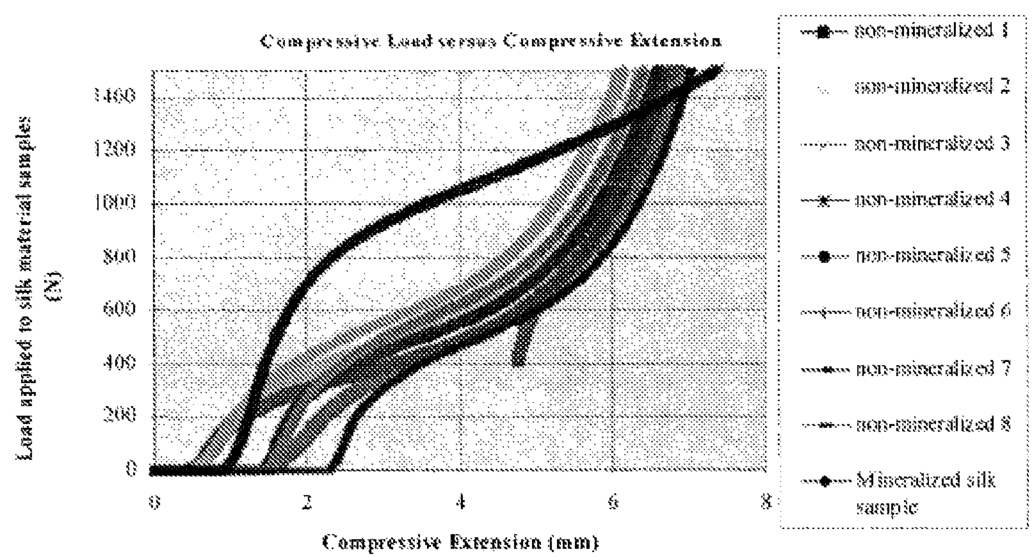
FIG. 10 is a graph that shows the compressive modulus of several exemplary non-mineralized and mineralized silk samples.

The silk fibers were processed through the sericin extraction step and were sliced into sections approximately 3 mm in length as shown in FIG. 10. A prototype of a mineralized silk block with approximately 2% of non-dissolved silk fibers by mass was made and is shown in FIG. 11. The silk fibers were not oriented in any particular direction, but were inserted into the silk-mineral mixture while it was being packed into the capsule.

J. Vacuum Pumping Step of Finished Samples to Accelerate Residual HFIP Removal

It was observed that completed samples of all forms of the silk polymer had the scent of HFIP after they had been removed from the hood. An additional processing step was to place completed samples in a vacuum chamber (see FIG. 12) for approximately 2 days. A few completed samples were placed in a vacuum pump at −25ATM. The scent of HFIP was reduced after this treatment, but was not completely eliminated. Another approach to avoid potential problems caused by residual solvent is to use an all-aqueous method that avoids the use of the organic solvent(s).

Example 2

Mechanical Properties of Silk/Hydroxyapatite Articles and Structures

A batch of 30% HA and non-mineralized silk polymer was packed into a cylindrical geometry during processing to determine the compressive modulus of the two materials.

Compressive modulus testing, as depicted in Table 1, demonstrated the relative benefit of adding mineral content to the silk polymer.

Another study conducted was to perform shear bond strength testing between the mineralized silk based biopolymer and dentin in natural extracted teeth using resin cement (Table 2). As a control, shear bond strength testing of bonded dental composite-resin buttons of similar dimensions bonded to dentin was also evaluated.

TABLE 1

Compressive modulus testing of Non-mineralized silk biopolymer, Mineralized silk biopolymer and commercially available dental composite resin restorative material (n = 24, 8/group), analyzed by one-way ANOVA.

| | Non-mineralized silk biopolymer | Mineralized silk biopolymer | Composite Resin |
|---|---|---|---|
| Mean Compressive Modulus (MPa) | 29.4 | 84.2 | 2793.1 |
| Standard Deviation (MPa) | 3.01 | 19.16 | 239.07 |
| ANOVA F-test | 1041.462 ($p < 0.0001$) | | |

TABLE 2

Shear bond strength testing of composite and mineralized silk polymer bonded to dentin (n = 16), analyzed by Independent Samples T-test.

| | Mineralized Silk bonded to Dentin | Composite bonded to Dentin |
|---|---|---|
| Mean (MPa) | 1.318 | 9.806 |
| Standard Deviation (MPa) | 0.616 | 3.980 |
| Independent Samples T-test | 5.961 ($p < 0.001$) | |

The invention claimed is:

1. An article of manufacture comprising:

(a) a mixture of silk fibroin polymer substantially free of sericin and hydroxyapatite particles, wherein (b) the mixture further comprises non-dissolved raw silk fibers that structurally reinforce the silk fibroin polymer, wherein said silk fibroin polymer is formed into an insoluble state about said hydroxyapatite particles in the presence of said hydroxyapatite particles.

2. The article of manufacture of claim 1, wherein said silk fibroin polymer and said hydroxyapatite particles are in substantially homogeneous admixture.

3. The article of manufacture of claim 1, wherein said article substantially retains the shape of a vessel in which it was formed.

4. The article of manufacture of claim 1, wherein said article comprises 0.1% to about 90% hydroxyapatite by weight.

5. The article of manufacture of claim 1, which further comprises a bioactive agent.

6. The article of manufacture of claim 5, wherein the bioactive agent is a selected from the group consisting of small molecules, nucleotides, carbohydrates, simple sugars, cells, peptides, proteins, glycoproteins, lipoproteins, antibodies, polysaccharides, nucleic acids, and combinations thereof.

7. The article of manufacture of claim 6, wherein the bioactive agent is selected from the group consisting of anti-infectives; chemotherapeutic agents; anti-rejection agents; analgesics; analgesic combinations; anti-inflammatory agents; hormones; growth factors; anti-angiogenic proteins; vitamins; sedatives; steroids; hypnotics; antibiotics; prostaglandins; radiopharmaceuticals; genes, anti-thrombotics, anti-metabolics; growth factor inhibitors; growth promoters; anticoagulants; antimitotics; fibrinolytics; anti-inflammatory steroids; monoclonal antibodies, and combinations thereof.

8. The article of manufactures of claim 1, wherein the article is an implantable structure.

9. The article of manufacture of claim 8, wherein the implantable structure is bioresorbed after implantation.

10. The article of manufacture of claim 8, wherein the implantable structure becomes integrated into bone following implantation.

11. The article of manufacture of claim 8, wherein the implantable structure facilitates bone healing or tooth structure or support.

12. The article of manufacture of claim 1, wherein said silk fibroin polymer in said insoluble state comprises primarily β-sheet conformation.

13. The article of manufacture of claim 1, wherein the non-dissolved raw silk fibers comprise sericin.

* * * * *